(12) United States Patent
Ashoori et al.

(10) Patent No.: US 10,390,752 B2
(45) Date of Patent: Aug. 27, 2019

(54) COGNITIVE CHAIR FOR MONITORING PARKINSON'S DISEASE PROGRESSION

(71) Applicant: International Business Machines Corporation, Armonk, NY (US)

(72) Inventors: Maryam Ashoori, White Plains, NY (US); Justin D. Weisz, Stamford, CT (US)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 37 days.

(21) Appl. No.: 15/274,472

(22) Filed: Sep. 23, 2016

(65) Prior Publication Data

US 2018/0085046 A1 Mar. 29, 2018

(51) Int. Cl.
*A61B 5/00* (2006.01)
*A61B 5/11* (2006.01)
*G16H 50/30* (2018.01)

(52) U.S. Cl.
CPC .......... *A61B 5/4082* (2013.01); *A61B 5/1116* (2013.01); *A61B 5/6891* (2013.01); *A61B 5/7275* (2013.01); *A61B 5/1101* (2013.01); *A61B 5/4842* (2013.01); *A61B 2562/0247* (2013.01); *G16H 50/30* (2018.01)

(58) Field of Classification Search
CPC ... A61B 5/1101; A61B 5/1116; A61B 5/1123; A61B 5/1124; A61B 5/4082; A61B 5/6891; A61B 2562/0247; A61B 2562/0252; A61B 5/4842
See application file for complete search history.

(56) References Cited

U.S. PATENT DOCUMENTS

| 7,461,896 | B2* | 12/2008 | Welles | A61B 5/11 297/217.3 |
| 8,469,884 | B2* | 6/2013 | David | A61B 5/0205 128/897 |
| 2013/0041290 | A1* | 2/2013 | Kording | A61B 5/1101 600/595 |
| 2014/0243709 | A1* | 8/2014 | Gibson | A61B 5/6892 600/587 |
| 2014/0371599 | A1* | 12/2014 | Wu | A61B 5/0077 600/476 |

FOREIGN PATENT DOCUMENTS

JP 2010154929 A * 7/2010 ............ A61G 5/00

OTHER PUBLICATIONS

Machine Translation of JP 2010-154929 A; translated by JPO; accessed Nov. 29, 2016; available from https://register.epo.org/ipfwretrieve?apn=JP.2008334469.A&lng=en.*

(Continued)

*Primary Examiner* — Devin B Henson
(74) *Attorney, Agent, or Firm* — Cantor Colburn LLP; Rahan Uddin (57) ABSTRACT

Embodiments include systems, methods, and computer program products for monitoring progression of Parkinson's disease. Aspects include receiving pressure data from a plurality of pressure sensors, the pressure sensors being positioned on a chair. Aspects also include analyzing the pressure data to determine the severity of a unified Parkinson's disease rating scale factor for a patient.

15 Claims, 7 Drawing Sheets

(56) References Cited

OTHER PUBLICATIONS

Stefanie D. Vassar, Yvette M. Bordelon, Ron D. Hays, et al., "Confirmatory Factor Analysis of the Motor Unified Parkinson's Disease Rating Scale," Parkinson's Disease, vol. 2012, Article ID 719167, 10 pages, 2012. https://doi.org/10.1155/2012/719167.*
http://www.img.medscape.com/fullsize/701/816/58977_UPDRS.pdf, accessed online Jul. 12, 2016, 8 pages.
http://www.journalofparkinsonsdisease.com/blog/palfreman/next-big-thing-monitoring-parkinson's-disease, accessed online Jul. 12, 2016, 2 pages.
http://www.pdf.org/en/Parkinson_Statistics, accessed online Jul. 12, 2016, two pages.
https://www.ibm.com/blogs/research/2016/06/ibms-cool-things-czar; 5 pages, accessed online Aug. 10, 2016.

* cited by examiner

COGNITIVE CHAIR FOR MONITORING PARKINSON'S DISEASE PROGRESSION

BACKGROUND

The present invention relates generally to monitoring progression of Parkinson's disease, and more specifically to methods, systems, and computer program products for monitoring progression of Parkinson's disease.

Parkinson's disease affects up to 1 million people in the United States. Doctors diagnose as many as 60,000 new cases each year. Parkinson's disease is a progressive condition. Symptoms can worsen, and over time new symptoms can appear. It can be difficult to estimate the rate at which Parkinson's will progress for a given individual. The progression of Parkinson's disease is commonly monitored through periodic visits to a physician to undergo unified Parkinson's disease rating scale (UPDRS) tests. The UPDRS tests assess and rate a number of categorized symptoms, including for instance daily living activities such as walking, tremor, and dressing, and motor skills such as speech, tremor at rest, action or postural tremor of hands, rigidity, postural stability, and arising from a chair. Comparisons with previous UPDRS results allow physicians to infer the progression of disease for a given patient.

SUMMARY

In accordance with one or more embodiments, a computer implemented method for assessing Parkinson's systems is provided. The method includes receiving, by a processor, pressure data from a plurality of pressure sensors, the pressure sensors being positioned on a chair. The method also includes analyzing, by the processor, the pressure data to determine the severity of a unified Parkinson's disease rating scale factor for a patient.

In accordance with another embodiment, a computer program product for assessing Parkinson's systems is provided. The computer program product includes a non-transitory storage medium readable by a processing circuit and storing instructions for execution by the processing circuit for performing a method including receiving, by a processor, pressure data from a plurality of pressure sensors, the pressure sensors being positioned on a chair. The method also includes analyzing, by the processor, the pressure data to determine the severity of a unified Parkinson's disease rating scale factor for a patient.

In accordance with a further embodiment, a processing system for assessing Parkinson's systems is provided. The processor is configured to receive pressure data from a plurality of pressure sensors, the pressure sensors being positioned on a chair. The processor is also configured to analyze the pressure data to determine the severity of a unified Parkinson's disease rating scale factor for a patient.

BRIEF DESCRIPTION OF THE DRAWINGS

The subject matter of embodiments of the invention is particularly pointed out and distinctly claimed in the claims at the conclusion of the specification. The foregoing and other features and advantages of the one or more embodiments described herein are apparent from the following detailed description taken in conjunction with the accompanying drawings in which:

DETAILED DESCRIPTION

It is understood in advance that although this description includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service. This cloud model can include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but can be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It can be managed by the organization or a third party and can exist on-premises or off-premises.

Community cloud: the cloud infrastructure is shared by several organizations and supports a specific community that has shared concerns (e.g., mission, security requirements, policy, and compliance considerations). It can be managed by the organizations or a third party and can exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure including a network of interconnected nodes.

Figure 1:
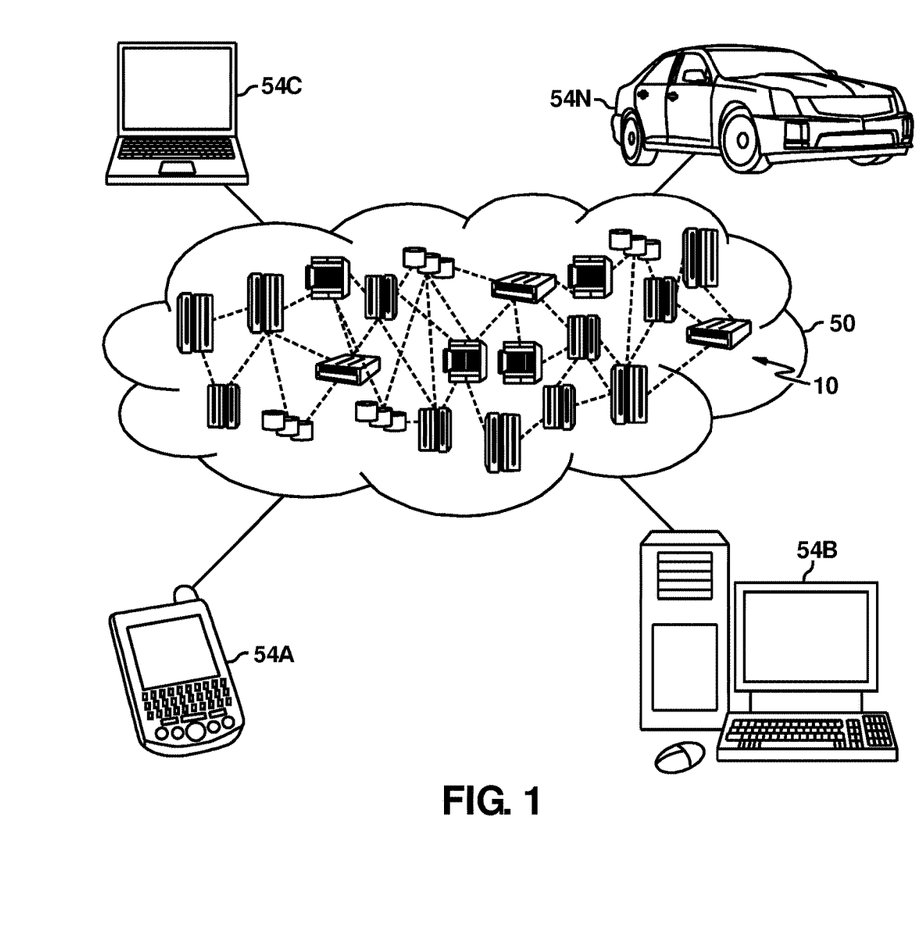
FIG. 1 depicts a cloud computing environment according to one or more embodiments of the present invention.

Referring now to FIG. 1, illustrative cloud computing environment 50 according to one or more embodiments of the present invention is depicted. As shown, cloud computing environment 50 includes one or more cloud computing nodes 10 with which local computing devices used by cloud consumers, such as, for example, personal digital assistant (PDA) or cellular telephone 54A, desktop computer 54B, laptop computer 54C, and/or automobile computer system 54N can communicate. Nodes 10 can communicate with one another. They can be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 1 are intended to be illustrative only and that computing nodes 10 and cloud computing environment 50 can communicate with any type of computerized device over any type of network and/or network addressable connection (e.g., using a web browser).

Figure 2:
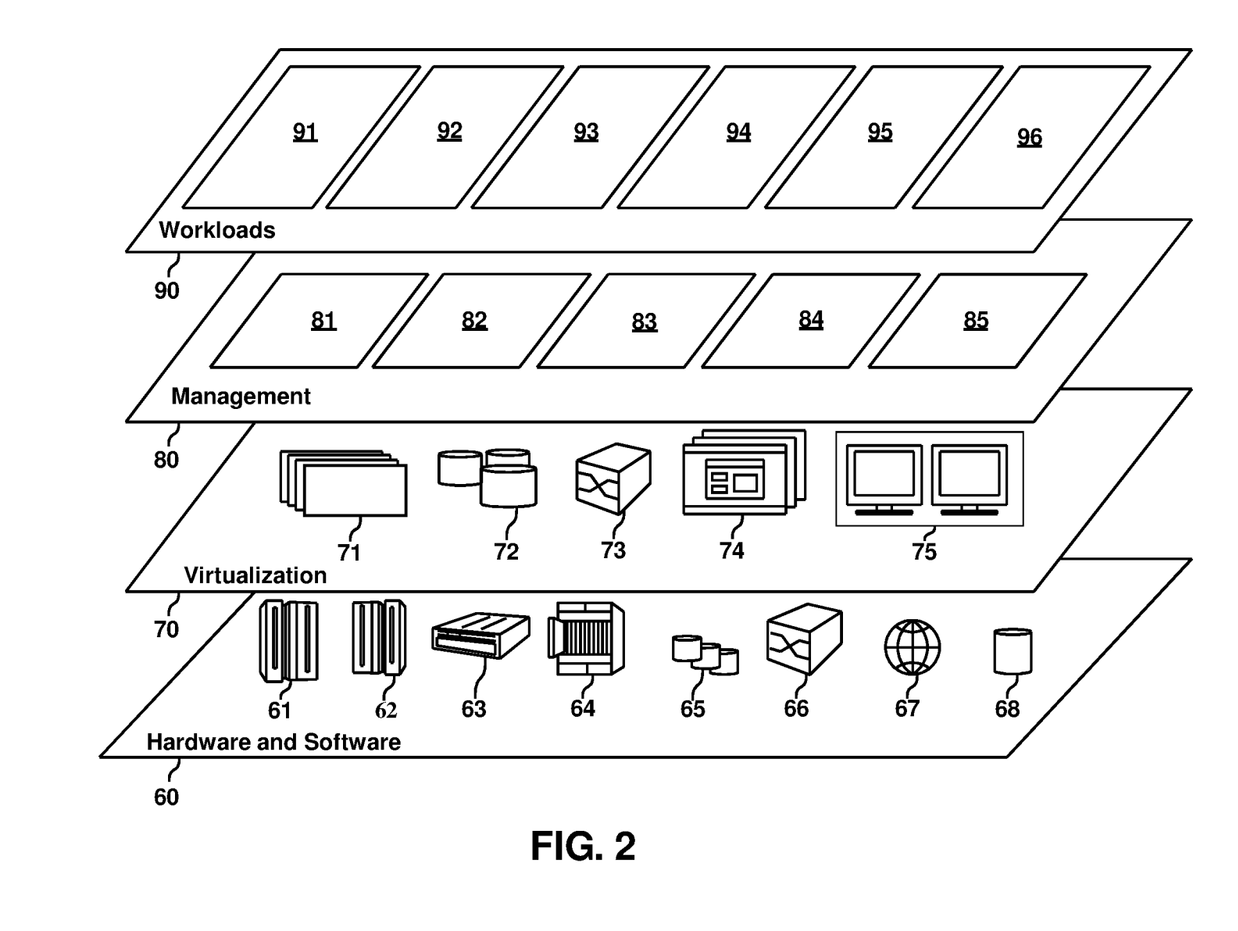
FIG. 2 depicts abstraction model layers according to one or more embodiments of the present invention.

Referring now to FIG. 2, a set of functional abstraction layers provided by cloud computing environment 50 (FIG. 1) according to one or more embodiments of the present invention is shown. It should be understood in advance that the components, layers, and functions shown in FIG. 2 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities can be provided: virtual servers 71; virtual storage 72; virtual networks 73, including virtual private networks; virtual applications and operating systems 74; and virtual clients 75.

In one example, management layer 80 can provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources can include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment can be utilized. Examples of workloads and functions which can be provided from this layer include: mapping and navigation 91; software development and lifecycle management 92; virtual classroom education delivery 93; data analytics processing 94; transaction processing 95; and medical data analysis 96 for monitoring progression of Parkinson's disease.

Figure 3:
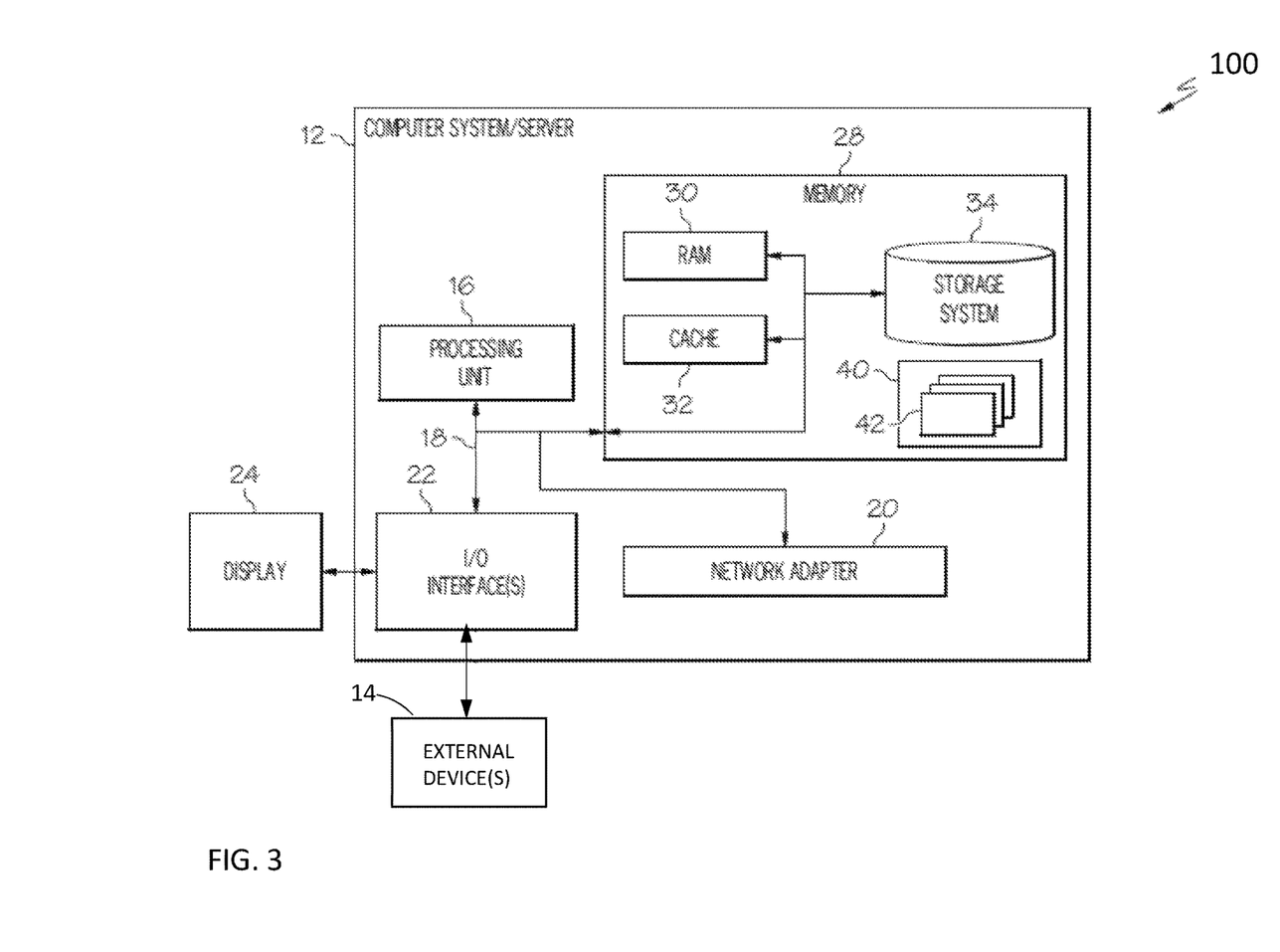
FIG. 3 depicts a computer system according to one or more embodiments of the present invention.

Referring now to FIG. 3, a schematic of a cloud computing node 100 included in a distributed cloud environment or cloud service network is shown according to one or more embodiments of the present invention. The cloud computing node 100 is only one example of a suitable cloud computing node and is not intended to suggest any limitation as to the scope of use or functionality of embodiments of the invention described herein. Regardless, cloud computing node 100 is capable of being implemented and/or performing any of the functionality set forth hereinabove.

In cloud computing node 100 there is a computer system/server 12, which is operational with numerous other general purpose or special purpose computing system environments or configurations. Examples of well-known computing systems, environments, and/or configurations that can be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 can be described in the general context of computer system-executable instructions, such as program modules, being executed by a computer system. Generally, program modules can include routines, programs, objects, components, logic, data structures, and so on that perform particular tasks or implement particular abstract data types. Computer system/server 12 can be practiced in distributed cloud computing environments where tasks are performed by remote processing devices that are linked through a communications network. In a distributed cloud computing environment, program modules can be located in both local and remote computer system storage media including memory storage devices.

As shown in FIG. 3, computer system/server 12 in cloud computing node 100 is shown in the form of a general-purpose computing device. The components of computer system/server 12 can include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnect (PCI) bus.

Computer system/server 12 typically includes a variety of computer system readable media. Such media can be any available media that is accessible by computer system/server 12, and it includes both volatile and non-volatile media, removable and non-removable media.

System memory 28 can include computer system readable media in the form of volatile memory, such as random access memory (RAM) 30 and/or cache memory 32. Computer system/server 12 can further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, memory 28 can include at least one program product having a set (e.g., at least one) of program modules that are configured to carry out the functions of embodiments of the invention.

Program/utility 40, having a set (at least one) of program modules 42, can be stored in memory 28 by way of example, and not limitation, as well as an operating system, one or more application programs, other program modules, and program data. Each of the operating system, one or more application programs, other program modules, and program data or some combination thereof, can include an implementation of a networking environment. Program modules 42 generally carry out the functions and/or methodologies of embodiments of the invention as described herein.

Computer system/server 12 can also communicate with one or more external devices 14 such as a keyboard, a pointing device, a display 24, etc., one or more devices that enable a user to interact with computer system/server 12, and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Turning now to an overview of embodiments of the present invention, systems and methodologies for assessing Parkinson's disease progression are described herein.

In embodiments, the unified Parkinson's disease rating scale (UPDRS) is utilized, which is the most commonly used scale in the clinical study of Parkinson's disease. The scale covers fourteen categories in which muscle operation can be affected by the disease, including speech, facial expressions, tremors, rigidity, finger tapping, hand movements, hand pronation or supination, foot tapping, ability to rise from a chair, posture, gait, and balance. An aggregate score between 0 and 108 is used to quantify a patient's motor condition and, over time, chart the progression of disease.

One assessment in the UPDRS test evaluates dyskinesia and a patient's ability to rise from a chair. In some embodiments, a chair is provided with pressure sensors on the seat and arm rests to assess various data associated with a patient's actions in arising from a chair. For example, the amount of time to rise from the chair, the amount of pressure placed on the sensors, and the relative pressure differential between sensors can provide quantitative assessments of a patient's ability to rise from a chair. Analysis of the output of the pressure sensors can also inform of the severity or frequency of tremors, patient rigidity, or can be used to analyze the patient's posture. Such objective or quantitative assessments can improve the quality of the physician's assessments, and accordingly, the diagnostic strength of the UPDRS measurements in monitoring the progression of disease in a given patient. Some embodiments include machine learning, allowing clinicians to automatically detect the posture of a patient, and determine whether a patient is experiencing a freezing episode while sitting in the chair and, thus, assess the progression of disease and monitor the progression over time.

Figure 4:
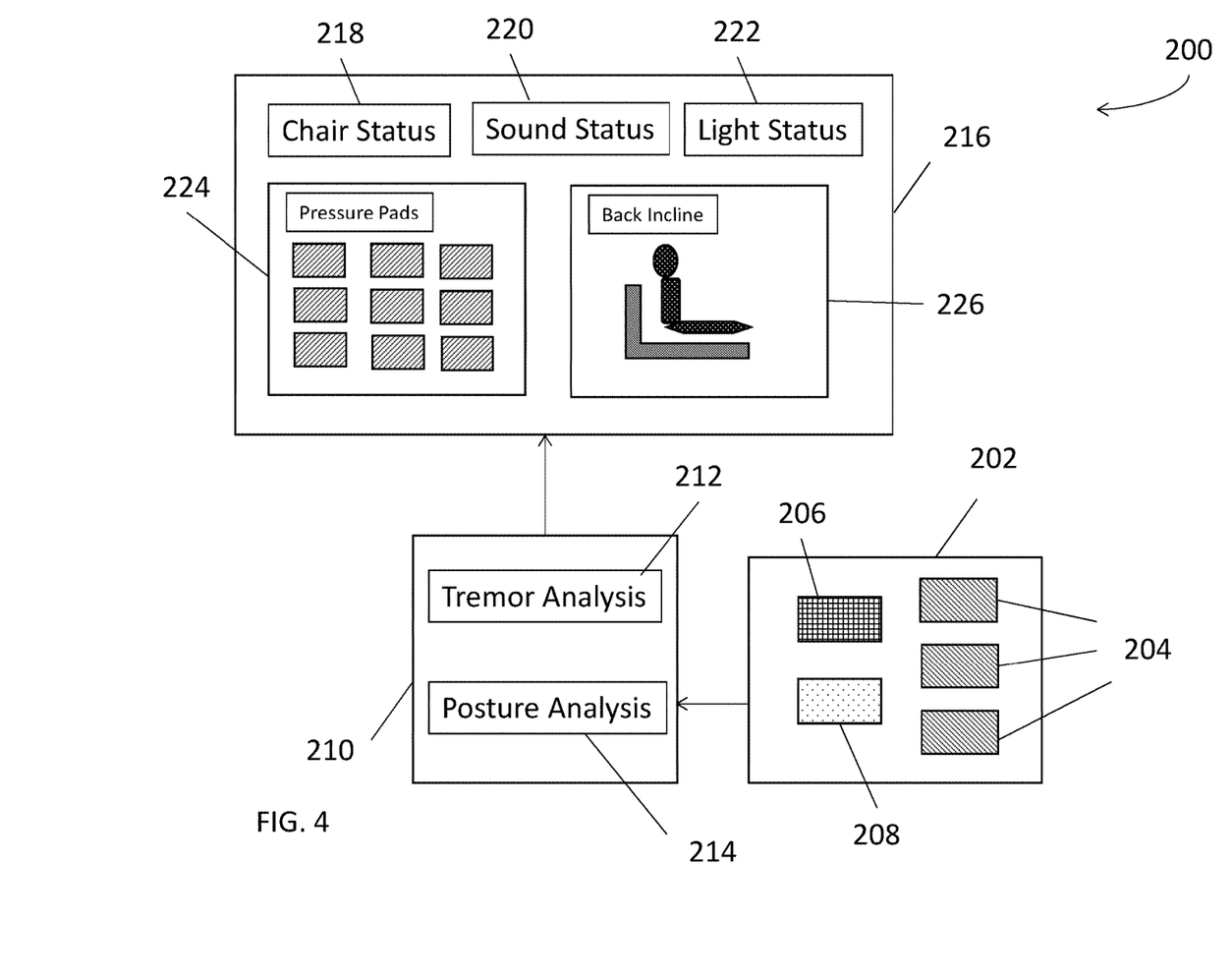
FIG. 4 illustrates an exemplary system for monitoring progression of Parkinson's disease according to one or more embodiments of the present invention.

Turning now to a more detailed description of one or more embodiments, FIG. 4 illustrates an exemplary system 200 for monitoring progression of Parkinson's disease according to one or more embodiments of the present invention. As is shown, system includes a chair 202 including a plurality of pressure sensors 204. Chair 202 can also include a biosensor 206 and a microphone 208. Chair 202 is in communication with a controller 210. The processor 210 can have a tremor analysis system 212. The controller 210 can also have a posture analysis system 214, as is shown. System can also include a display 216. The display 216 can show any information relevant to the assessment of Parkinson's disease. As illustrated, for example, the display 216 can show the chair status 218, the sound status 220, the light status 222, for example the light level of the room, and the state of each pressure pad 224. The display can also show posture data 226 derived from the pressure sensors 204.

Biosensors 206 can also be included in the chair 204. In some embodiments, not shown, biosensors 206 can be included in the system 200 in location other than on the chair. Biosensors 206 can provide any biological or biophysical information that can be used by clinicians in an assessment of Parkinson's disease or the Parkinson's disease assessment, including, for instance, indicators of a high stress or anxiety level that can contribute to the presence of one or more Parkinson's symptoms. For example, biosensors can include heart rate monitors, pulse oximeters, blood pressure monitors, thermometers, EKG instrumentation, respiration monitors, and the like.

Microphone 208 can be provided in the system 200, for example on the chair 202. A microphone 208 can, for example, measure the ambient noise level in the room to provide a clinician with optimal assessment conditions. In some cases, higher levels of noise can increase a patient's tremors. In some embodiments, the noise level obtained from microphone 208 can be correlated with patient tremor data.

Controller 210 can include a microprocessor. In some embodiments, controller 210 includes an Arduino controller. In some embodiments, controller 210 includes Raspberri Pi. Controller 210 can include any microcontroller suitable for analyses described herein, such as MSP430 LaunchPad, Nanode, Pinguino PIC32, STM32 Discovery, or Teensy 2.0. Controller 210 can be in communication with the chair 204 wirelessly or wired, and can obtain and report data through Wi-Fi, Bluetooth, or any other means.

Controller 210 can perform one or more analyses pertaining to assessment of pressure sensor data. In some embodiments, controller 210 includes a posture analysis system 214.

Figure 5:
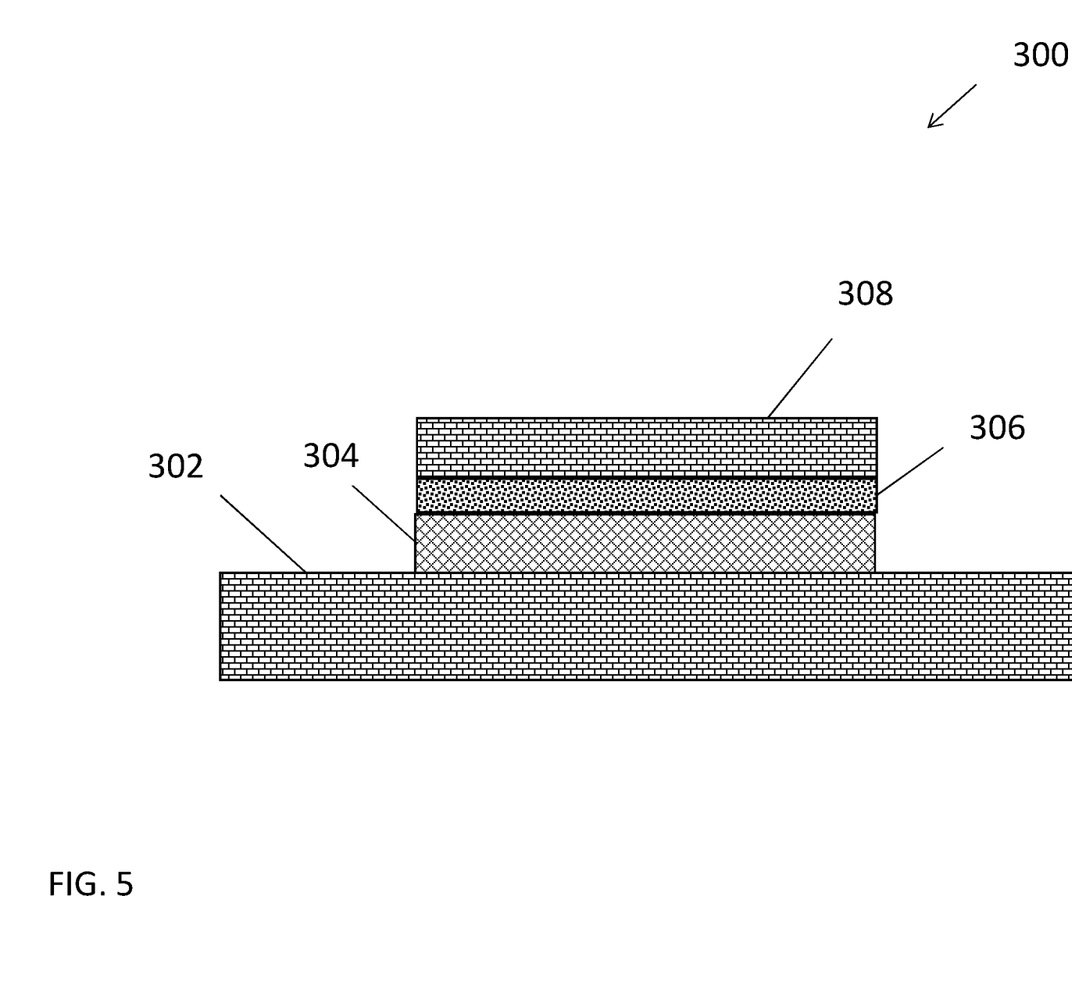
FIG. 5 illustrates a cross-sectional side view of an exemplary chair portion including a pressure sensor according to one or more embodiments of the present invention.

FIG. 5 illustrates a cross-sectional side view of an exemplary chair portion 300 including a pressure sensor according to one or more embodiments of the present invention. A first layer of conductive fabric 304 can be positioned on the surface of a chair 302. A layer of pressure sensitive electrically conductive material, such as Velostat 306 can be positioned between the first layer of conductive fabric 304 and a second layer of conductive fabric 308. Conductive fabric 304 and 308 includes any textile which can conduct electricity, such as textiles woven with metal strands or textiles coated or embedded with electrically conductive elements, such as carbon, nickel, copper, gold, silver or titanium. Exemplary textile substrates include, for instance, cotton, polyester, nylon, and stainless steel.

Pressure sensors 204 can sense the presence and relative amount of pressure. Pressure sensors 204 can be included in a chair 204 in a variety of positions and in a variety of locations. In some embodiments, a plurality of pressure sensors 204 are placed on the seat of the chair 204. In some embodiments, a chair contains at least six pressure sensors. In some embodiments, a chair contains 8 pressure sensors. In some embodiments, a chair contains 10 pressure sensors. For example, a chair 204 can contain six pressure sensors on a seat and two pressure sensors on the armrests. In some embodiments, a plurality of pressure sensors 204 are placed on the armrest of the chair 204. For example, pressure sensors 204 on an armrest can provide useful information in a Parkinson's progression analysis as a patient attempts to rise from the chair and places pressure on an armrest to assist with standing up. Pressure sensors 204 can be a variety of sizes and shapes depending on the type, quality, and quantity of data desired.

Figure 6:
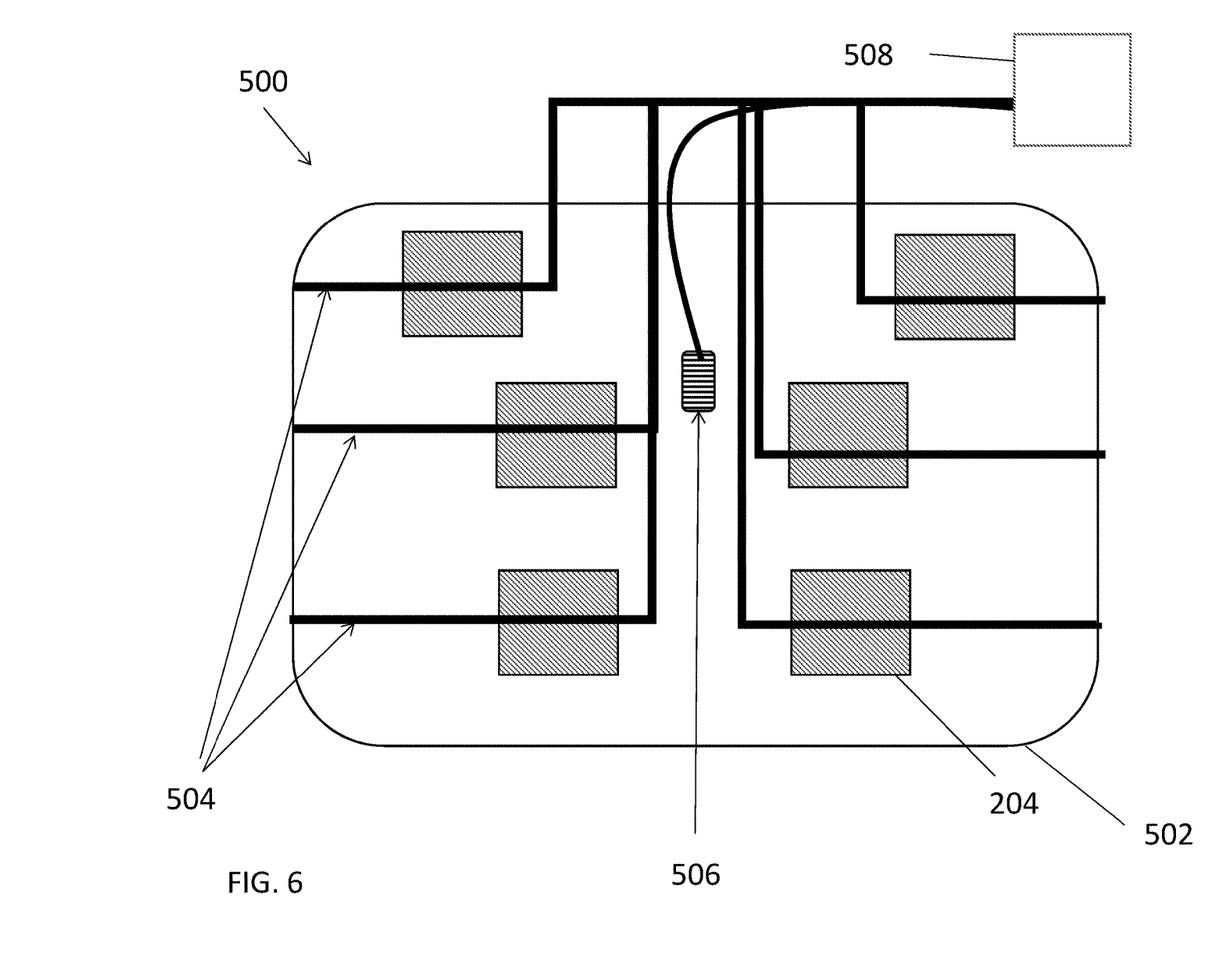
FIG. 6 illustrates a bottom view of a chair seat cushion for monitoring progression of Parkinson's according to one or more embodiments of the present invention.

FIG. 6 illustrates a bottom view of a chair seat cushion 500 for monitoring progression of Parkinson's according to one or more embodiments of the present invention. Chair seat cushion 500 includes a surface 502, upon which a plurality of pressure sensors 204 can be placed. The pressure sensors 204 can be connected via wire to an output 508. The chair seat cushion can also contain a microphone 506 connected to the output 508.

Figure 7:
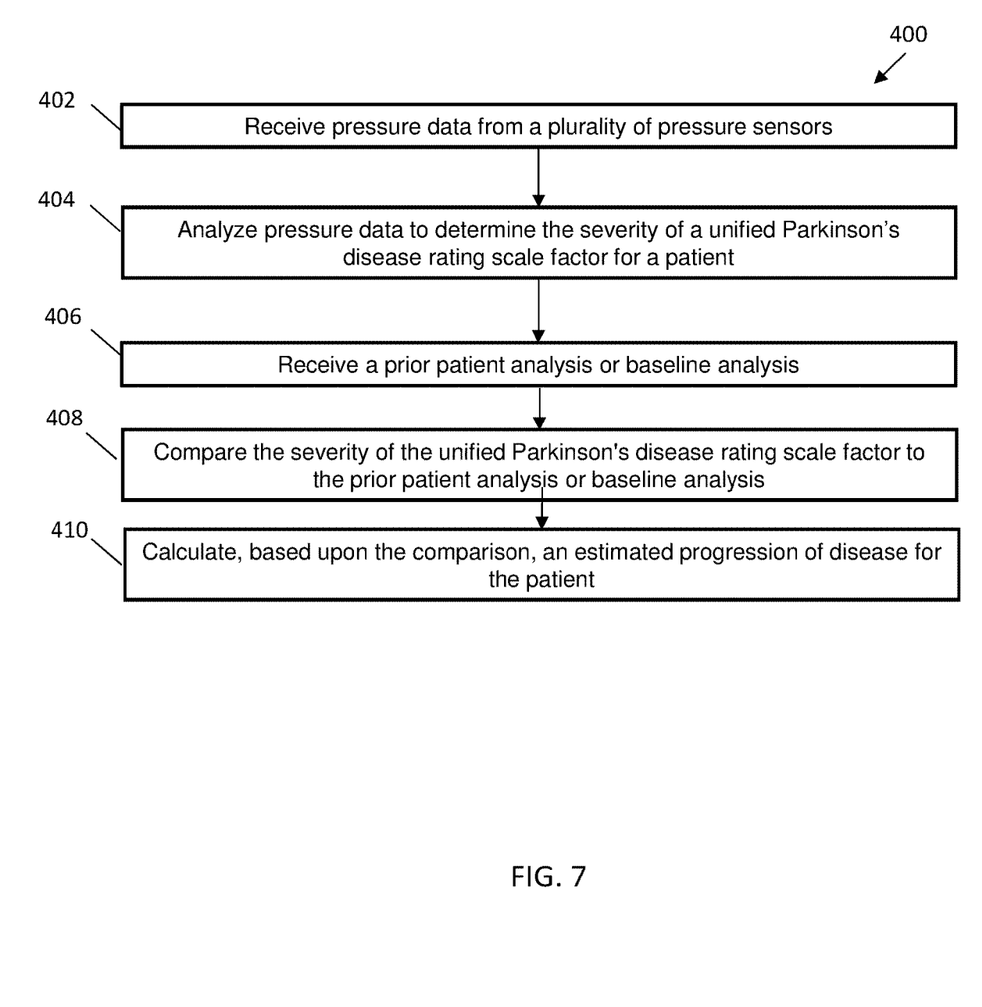
FIG. 7 is a flow diagram illustrating an exemplary method of monitoring progression of Parkinson's disease according to one or more embodiments of the present invention.

FIG. 7 is a flow diagram illustrating an exemplary method 400 of monitoring progression of Parkinson's disease according to one or more embodiments of the present invention. The method 400 includes, as shown at block 402 receiving pressure data from a plurality of pressure sensors. The method 400 also includes, as shown at block 404, analyzing pressure data to determine the severity of a UPDRS factor for a patient. The method 400 also includes receiving a prior patient analysis or baseline analysis, as shown at block 406. The method also includes, as shown at block 408, comparing the severity of the UPDRS factor to the prior patient analysis or baseline analysis. The method 400 also includes, as shown at block 410, calculating, based upon the comparison, an estimated progression of disease for the patient.

In some embodiments, the UPDRS factor includes the time for the patient to rise from the chair. In some embodiments, the UPDRS factor includes tremor data, such as a severity of tremors or a frequency of tremors. In some embodiments, the UPDRS factor includes patient posture. For example, methods include analyzing pressure data to determine a tilt or slant to a posture or the degree to which a patient is leaning in a direction.

Analysis can include utilization of a machine learning model to classify the degree to which the patient is experiencing a symptom, such as dyskinesia or tremors. In some embodiments, deep learning models or support vector machines (SVMs) are used. Output of the analysis can be provided to a clinician in any manner, including to a display.

In some embodiments, a system for assessment of Parkinson's disease is provided. The system includes a chair. The system also includes a plurality of pressure sensors positioned on the chair, each of the plurality of pressure sensors including a first conductive fabric layer, a velostat layer, and a second conductive fabric layer. The system also includes a controller device. In some embodiments, the system includes a microphone. In some embodiments, the system includes a biosensor. In some embodiments, the pressure sensors are positioned on the seat of a chair. In some embodiments, the pressure sensors are positioned on the armrest of a chair.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, element components, and/or groups thereof.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form described. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The flow diagrams depicted herein are just one example. There can be many variations to this diagram or the steps (or operations) described therein without departing from the spirit of embodiments of the invention. For instance, the steps can be performed in a differing order or steps can be added, deleted or modified. All of these variations are considered a part of the claimed invention.

The descriptions of the various embodiments of the present invention have been presented for purposes of illustration, but are not intended to be exhaustive or limited to the embodiments described. Many modifications and variations will be apparent to those of ordinary skill in the art without departing from the scope and spirit of the described embodiments. The terminology used herein was chosen to best explain the principles of the embodiments, the practical application or technical improvement over technologies found in the marketplace, or to enable others of ordinary skill in the art to understand the embodiments described herein.

What is claimed is:

1. A computer-implemented method for assessing Parkinson's symptoms, the method comprising:
    receiving, by a processor, pressure data from a plurality of pressure sensors, at least some of the plurality of pressure sensors are positioned on a seat of a chair and comprise a first conductive fabric layer, a layer of pressure sensitive electrically conductive material, and a second conductive fabric layer,
    analyzing, by the processor, the pressure data to determine the severity of a unified Parkinson's disease rating scale factor for a patient, wherein analyzing the pressure data comprises classifying a degree to which the patient is experiencing a symptom with a machine learning model,
    receiving, by the processor, a prior patient analysis, the prior patient analysis comprising a prior unified Parkinson's disease rating scale factor for the patient,
    comparing, by the processor, the prior patient analysis to the severity of the unified Parkinson's disease rating scale factor,
    calculating, based upon the comparison, an estimated progression of disease for the patient, and
    outputting, to a user interface of a display, the pressure data, a sound status indicator comprising an ambient noise level, and a light status indicator comprising a light level.

2. The computer-implemented method of claim 1, wherein the unified Parkinson's disease rating scale factor comprises the patient's ability to rise from a chair.

3. The computer-implemented method of claim 2, the method comprising calculating, based upon the pressure data, a time for the patient to rise from the chair.

4. The computer-implemented method of claim 1, the method comprising calculating, based upon the pressure data, a severity of tremors.

5. The computer-implemented method of claim 1, the method comprising determining, based upon the pressure data, a posture of the patient and comparing the posture of the patient to a baseline posture.

6. The computer-implemented method of claim 1, wherein each of the severity of the unified Parkinson's disease rating scale factor for the patient and the prior unified Parkinson's disease rating scale factor comprises an aggregate score between 0 and 108.

7. The computer-implemented method of claim 1, wherein the chair further comprises a biosensor.

8. A computer program product for assessing Parkinson's symptoms, the computer program product comprising:
    a computer readable storage medium readable by a processing circuit and storing program instructions for execution by the processing circuit for performing a method comprising:
    receiving pressure data from a plurality of pressure sensors, at least some of the plurality of pressure sensors are positioned on a seat of a chair and comprise a first conductive fabric layer, a layer of pressure sensitive electrically conductive material, and a second conductive fabric layer,
    analyzing the pressure data to generate the severity of a unified Parkinson's disease rating scale factor for a patient, wherein analyzing the pressure data comprises classifying a degree to which the patient is experiencing a symptom with a machine learning model,
    receiving a prior patient analysis, the prior patient analysis comprising a prior unified Parkinson's disease rating scale factor for the patient,
    comparing the prior patient analysis to the severity of the unified Parkinson's disease rating scale factor,
    calculating an estimated progression of disease for the patient, and
    outputting, to a user interface of a display, the pressure data, a sound status indicator comprising an ambient noise level, and a light status indicator comprising a light level.

9. The computer program product of claim 8, wherein software is provided as a service in a cloud environment.

10. The computer program product of claim 8, wherein the unified Parkinson's disease rating scale factor comprises the patient's ability to rise from a chair.

11. The computer program product of claim 10, the method comprising calculating, based upon the pressure data, a time for the patient to rise from the chair.

12. The computer program product of claim 8, the method comprising calculating, based upon the pressure data, a severity of tremors.

13. The computer program product of claim 8, the method comprising determining, based upon the pressure data, a posture of the patient and comparing the posture of the patient to a baseline posture.

14. A processing system for assessing Parkinson's symptoms, comprising:
    a processor in communication with one or more types of memory, the processor configured to:

receive pressure data from a plurality of pressure sensors, at least some of the plurality of pressure sensors are positioned on a seat of a chair and comprise a first conductive fabric layer, a layer of pressure sensitive electrically conductive material, and a second conductive fabric layer;

analyze the pressure data to determine the severity of a unified Parkinson's disease rating scale factor for a patient, wherein analyzing the pressure data comprises classifying a degree to which the patient is experiencing a symptom with a machine learning model;

receive a prior patient analysis, the prior patient analysis comprising a prior unified Parkinson's disease rating scale factor for the patient;

compare the prior patient analysis to the severity of the unified Parkinson's disease rating scale factor;

calculate an estimated progression of disease for the patient; and output, to a user interface of a display, the pressure data, a sound status indicator comprising an ambient noise level, and a light status indicator comprising a light level.

15. The processing system of claim 14, wherein the unified Parkinson's disease rating scale factor comprises the patient's ability to rise from the chair.

* * * * *